United States Patent
Jensen

(10) Patent No.: US 6,666,579 B2
(45) Date of Patent: Dec. 23, 2003

(54) METHOD AND APPARATUS FOR OBTAINING AND DISPLAYING COMPUTED TOMOGRAPHY IMAGES USING A FLUOROSCOPY IMAGING SYSTEM

(75) Inventor: Vernon Thomas Jensen, Draper, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 244 days.

(21) Appl. No.: 09/752,791

(22) Filed: Dec. 28, 2000

(65) Prior Publication Data

US 2002/0085681 A1 Jul. 4, 2002

(51) Int. Cl.$^7$ ................................................ H05G 1/02
(52) U.S. Cl. ............................................ 378/197; 378/62
(58) Field of Search .......................... 378/197, 62, 198, 378/205

(56) References Cited

U.S. PATENT DOCUMENTS

| | | | |
|---|---|---|---|
| 4,797,907 A | 1/1989 | Anderton | 378/101 |
| 5,251,635 A | 10/1993 | Dumoulin et al. | 128/653 |
| 5,544,217 A * | 8/1996 | Kadowaki et al. | 378/193 |
| 5,873,822 A | 2/1999 | Ferre et al. | 600/407 |
| 6,079,876 A * | 6/2000 | Schuetz | 378/205 |
| 6,206,566 B1 * | 3/2001 | Schuetz | 378/205 |
| 6,285,902 B1 * | 9/2001 | Kienzle et al. | 378/20 |
| 6,533,455 B2 * | 3/2003 | Graumann et al. | 378/205 |

FOREIGN PATENT DOCUMENTS

| | | | |
|---|---|---|---|
| DE | 199 17 867 A1 | 11/2000 | |
| EP | 917855 A1 * | 5/1999 | ............ A61B/6/00 |
| WO | WO 00/64367 | 11/2000 | |

OTHER PUBLICATIONS

International Search Report for application No. PCT/US01 48128 dated May 31, 2002.

* cited by examiner

*Primary Examiner*—David V. Bruce
*Assistant Examiner*—Courtney Thomas
(74) *Attorney, Agent, or Firm*—McAndrews, Held & Malloy, Ltd.; Peter J. Vogel; Michael A. Dellapenna

(57) ABSTRACT

A medical imaging system is provided for diagnostic and interventional procedures. The system includes a C-arm having an x-ray source and a receptor for obtaining fluoroscopic images of a patient. The C-arm is moved through an image acquisition path (A, B), along which at least first and second images are obtained. An acquisition module obtains multiple 2-D fluoroscopic images at desired positions along the image acquisition path and an image processor constructs a 3-D volume of object data based on the 2-D fluoroscopic images. Patient information is displayed based upon the 3-D volume of patient information. A position tracking system is included to track the position of the receptor, patient and (if included) a surgical instrument. The position information is used to control the time at which exposures are obtained and (if included) to superimpose instrument graphical information on a display with patient information.

34 Claims, 5 Drawing Sheets

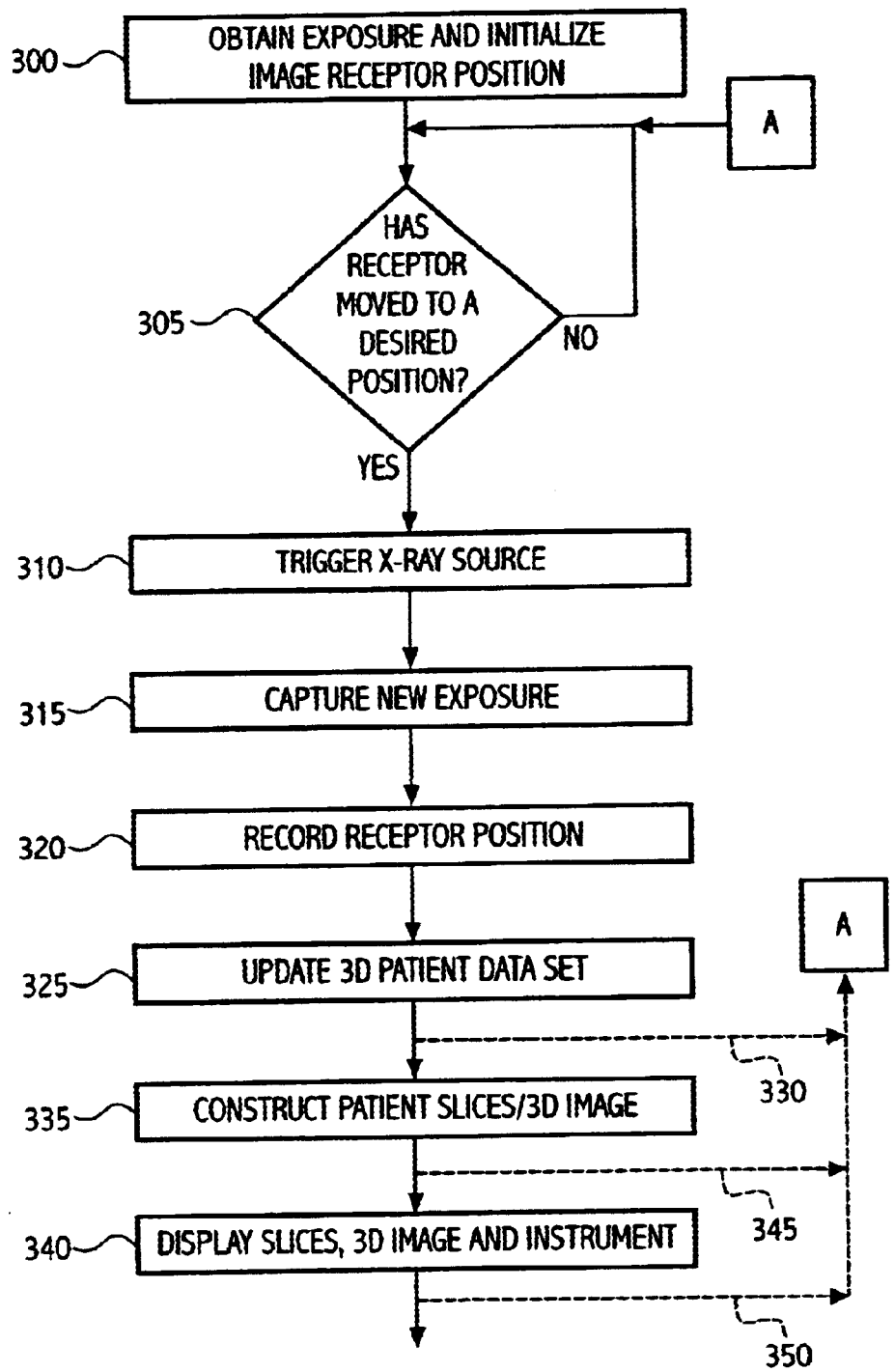

METHOD AND APPARATUS FOR OBTAINING AND DISPLAYING COMPUTED TOMOGRAPHY IMAGES USING A FLUOROSCOPY IMAGING SYSTEM

CROSS REFERENCE TO RELATED APPLICATIONS (if applicable)

Not applicable.

STATEMENT REGARDING FEDERALLY SPONSORED RESEARCH & DEVELOPMENT (if applicable)

Not applicable

BACKGROUND OF THE INVENTION

The preferred embodiments of the present invention generally relate to a mobile C-arm based x-ray system for constructing three dimensional (3-D) volumetric data sets and using the data sets in diagnostic and interventional medical procedures. More specifically, at least one preferred embodiment of the present invention relates to a mobile C-arm based x-ray medical imaging system that constructs three-dimensional volumetric data sets of digital x-ray images, based, in part, on coordinate information for patients and the x-ray receptor, and uses the data sets for diagnostic and interventional procedures to be carried out.

Conventional medical imaging modalities, such as computed tomography (CT) and magnetic resonance imaging (MRI), use sophisticated mechanical gantry structures to support patients and equipment used to construct patient imaging data sets. The CT and MRI data sets are formed from a plurality of scans in which the exact position of the patient is known from the relation between the mechanical gantry and the patient table formed integral with the gantry. For instance, CT systems use a circular gantry that supports a continuously rotating fan beam x-ray source and an opposed arcuate detector array. The fan beam x-ray source and detector array continuously rotate within the gantry. The CT system also includes a patient table integral with the gantry. The table moves the patient through the gantry at predefined incremental steps while the fan beam x-ray source continuously rotates. The mechanical interconnection of the gantry and table in the CT system maintain a known relationship between the position of the patient and of the x-ray source and detector array at all times, and thus is able to construct a set of 2-D images aligned in a known relationship to one another in order to construct a 3-D volumetric data set of the images. Once the 3-D volume is constructed, individual slices of the patient may be obtained to present to the doctor desired views, such as the sagittal, coronal and axial views; or segmented or rendered image views. MRI systems maintain a similar mechanical interconnection between the gantry holding the magnet coils and patient table.

However, CT and MR systems are extremely complex, large and expensive. In the more recent history, intraoperative MR and mobile CT systems have been proposed. However, these intraoperative MR and mobile CT systems still require a configuration comprising a patient table formed integrally with the gantry. Many intraoperative and diagnostic procedures do not justify or warrant the cost of MR and CT systems, mobile or otherwise. Further, intraoperative MR and mobile CT systems are still quite large and take up a significant portion of an operating room.

Today, many diagnostic and surgical procedures are carried out using a mobile C-arm type x-ray system in a fluoroscopy or digital spot mode. Mobile C-arm x-ray systems are more commonly found in an OR or interoperative hospital and clinical facilities as such systems are much smaller, less complex and less expensive than CT and MR systems. Conventional mobile C-arm systems have been used during surgical procedures by performing standard fluoroscopic x-ray imaging to acquire one or more x-ray images of the patient during the procedure. The most common x-ray images obtained using the mobile C-arm include the AP and lateral views. By way of an example, during a surgical planning phase, the doctor may obtain two exposures/shots, namely one AP view and one lateral view to initially observe and study the region of interest. In a spinal procedure, the doctor next will resect tissue from the region of interest (ROI) to expose a bony portion of interest. Next, the doctor places the surgical instrument or tool near the bony portion of interest, with the instrument or tool located at a desired position and orientation at which the doctor desires to carry out the surgical procedure. The doctor next typically obtains two new exposures/shots (AP and lateral) of the ROI and instrument to view the position and orientation of the instrument/tool relative to the bony portion of interest. Then the doctor begins the surgical procedure, such as drilling a hole in the bone or the like. At various stages along the surgical procedure, the doctor obtains new pairs of exposures/shots (AP and lateral) to determine the progress of the procedure. This process is repeated until the tool reaches a desired destination. The foregoing process requires several exposures to be taken of the patient, thereby causing the patient to receive a large x-ray dose, even though it is preferable to minimize the radiation dosage required to complete a procedure.

C-arm based systems have a configuration of joints and interconnects that permit the doctor to move and rotate the C-arm through several directions of movement, such as an orbital tracking direction, longitudinal tracking direction, lateral tracking direction, transverse tracking direction, pivotal tracking direction, and "wig-wag" tracking direction. The C-arm may be moved through each of the foregoing tracking directions by releasing mechanical locks at the appropriate joints and interconnects.

At least one C-arm type system has been proposed that includes a mechanical motor to drive the C-arm (and thus the x-ray source and image intensifier) in the orbital tracking direction, namely in an arcuate path within the plane defined by the C-arm frame. As the motor moves the C-arm in the orbital tracking direction, a series of exposures are taken. The series of exposures are combined into a data set for display as a three-dimensional volume. However, the motor driven C-arm system is only useful for diagnostic procedures, not interventional operations, since the image frames are not correlated to the patient location and alignment.

A need remains for an improved C-arm based system capable of constructing 3-D volumetric data sets of patient and instrument information and capable of displaying slices, segments or rendered volumes of data at any desired viewing angle for use during diagnostic and interventional procedures.

BRIEF SUMMARY OF THE INVENTION

According to one aspect of a preferred embodiment, a medical imaging system is provided having a C-arm with an x-ray source for generating x-rays and a receptor device for receiving x-rays and deriving a fluoroscopic image from the x-rays received. The C-arm moves the x-ray source and receptor device along an image acquisition path between at least first and second image acquisition positions. An acquisition module obtains a series of 2-D fluoroscopic images, wherein first and second fluoroscopic images are obtained when the x-ray source and receptor are located at the first and second image acquisition positions, respectively. An image processor constructs a 3-D volume of object voxels based on the series of fluoroscopic images. A monitor displays images based on the 3-D volume, such as 3D renderings, patient slices and the like. A position tracker monitors the position of the C-arm and patient at each of the positions through the series of exposures and provides position information for the patient and the receptor for fluoroscopic images. The C-arm may be manually, mechanically or automatically moved along the image acquisition path.

According to at least one alternative embodiment, an image processor constructs a computed tomography volume from a series of 2-D fluoroscopic images. The image processor transforms multiple 2-D fluoroscopic images into 3-D volumetric data sets. The image processor may perform an iterative reconstruction technique to construct the 3-D volume. Alternatively, the image processor may perform a back projection technique to construct the 3-D volume.

According to at least one alternative embodiment, the C-arm is rotatably mounted to a base that moves the C-arm along an orbital rotation path to cause the x-ray source and receptor device to follow an arc about an orbital axis aligned perpendicular to a plane defined by the C-arm. According to at least one alternative embodiment, a mobile base is provided having wheels. The C-arm may be mounted to the base and the base may be movable on the wheels along a lateral rotation arc formed tangentially to an orbital axis traversing the C-arm plane to move the x-ray source and receptor device along a lateral image acquisition path between the first and second positions. A pivot member may be provided. The pivot member may pivot the C-arm about a pivot axis contained in and extending along the plane containing the C-arm. The pivot member pivots the x-ray source and receptor device about a pivotal image acquisition path between the first and second positions.

According to a further alternative embodiment, the acquisition module acquires a sequence of 2-D fluoroscopic images at predetermined positions spaced along the imaging path. Optionally, the acquisition module may obtain 2-D fluoroscopic images at an even interval along the image acquisition path. The even interval may be at approximately every five degrees of rotation of the C-arm. The acquisition module continuously calculates the position of the C-arm with respect to a coordinate reference system and triggers the x-ray source to generate exposures when the C-arm reaches predetermined positions along the imaging path.

In one embodiment, the first and second positions may constitute the beginning and ending positions, respectively, along an arcuate range of motion of the C-arm. The beginning and ending positions may be between 145 degrees and 190 degrees apart.

The preferred embodiments of the present invention may be used in a variety of diagnostic procedures, interventional surgical applications and the like, such as in orthopedic procedures, spinal studies and applications, joint replacement procedures and the like. A spinal application may involve attaching a pen or screw to a vertebra, such as the cervical, thoracic or lumbar. The vertebra represents a complex anatomy that may not be satisfactorily illustrated through AP and lateral fluoroscopy views. The AP and lateral views may not necessarily show adequate intricate detail of the vertebra. Preferably, spinal applications involve the display of sagittal, coronal and axial views to present the cross-section of the spinal column in a slice by slice format. According to at least one preferred embodiment, sagittal, coronal and axial views may be obtained from the 3-D volume data set obtained by the C-arm.

As the doctor performs the spinal surgery, the instrument or tool may be superimposed upon one or more of the 2-D or 3-D images presented to the doctor. The position of the instrument or tool is continuously and repeatedly updated in real-time in order to follow the movement of the instrument or tool relative to the patient's spinal column.

An example of a general orthopedic procedure, in which at least one preferred embodiment of the present invention may be used, involves fracture reduction, such as when setting a broken bone. During a fracture reduction operation, one or more tracking devices may be attached to one or more points on the fractured bone. The 2-D or 3-D images obtained illustrating the fractured bone may be used for surgical planning and/or alignment. The 2-D or 3-D images may further be used during implementation of the fracture reduction procedure (i.e. set the bone) to obtain views in any desired orientation of the fractured bones. As the fracture is closed, the 2-D or 3-D images may be viewed in any desired orientation to determine if the bones are being properly aligned.

Another example of a general orthopedic procedure, in which at least one preferred embodiment of the present invention may be used, involves joint replacement, such as when replacing a knee with a prosthesis. A knee prosthesis includes a ball and receiving joint. A notch is cut in the bone on one side of the knee and the ball is inserted therein. A notch is cut in the bone on the other side of the knee and the receiving joint is inserted therein. It is important that the ball and receiving joint be properly aligned within the bone notches since if either is misaligned by a few degrees, the foot will not be aligned properly. Also, misalignment within the ball and joint causes the prosthesis to prematurely wear out since the joints are designed to have an equal load. If the load is unbalanced by only a few degrees, the joint will wear prematurely.

General orthopedic and spinal procedures are not considered to warrant the need for a computed tomography system, nor justify the cost added to the operation for a CT system. However, typically, fluoroscopy systems are present in, or available to, most operating rooms and thus more readily available for used during general orthopedic and spinal procedures. Volumetric reconstruction with the fluoroscope affords the doctor the ability to conduct surgical planning quickly while a patient is anesthetized on the table. Within a few minutes of the surgical planning phase (e.g. preoperative planning), the doctor is able to execute the plan to afford proper alignment (e.g. interoperative navigation) and to verify quality assurance. Hence, at least one preferred embodiment of the present invention enables a doctor to verify that a plan has been properly executed. In accordance with at least one preferred embodiment of the present invention, imaging data may be collected during an intraoperative procedure (e.g. interoperative data collection), without any need for pre-imaging. By affording interoperative data collection, a patient need not be moved to a separate room for image collection, but instead, the images may be obtained by the C-arm while the patient is anesthetized and prepped for surgery.

BRIEF DESCRIPTION OF THE DRAWINGS

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

FIG. 8 illustrates a flow chart of the steps carried out in accordance with at least one preferred embodiment of the present invention.

DETAILED DESCRIPTION OF THE INVENTION

Figure 1:
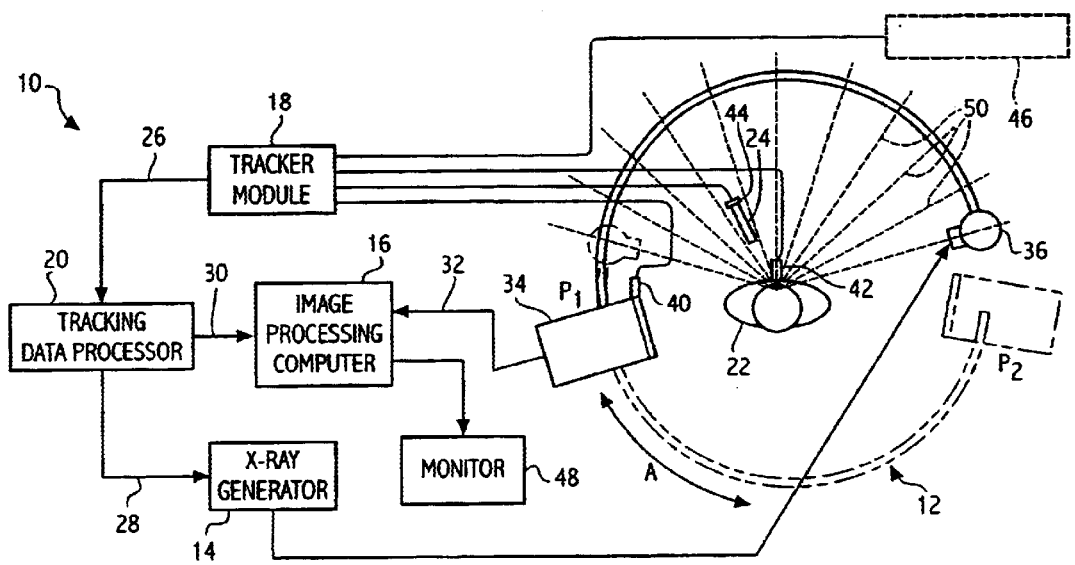
FIG. 1 illustrates a block diagram of a fluoroscopic imaging system formed in accordance with a preferred embodiment of the present invention.

FIG. 1 illustrates a fluoroscopy x-ray system 10 that includes a C-arm 12 that is electrically connected to an x-ray generator 14, an image processing computer 16 and a tracker module 18. The tracker module 18 communicates with a tracking data processor 20 which in turn communicates with the image processing computer 16 and x-ray generator 14. The image processing computer 16 communicates with a monitor 48.

The C-arm 12 includes an x-ray source 36 mounted to one side and an x-ray receptor device 34 mounted to the opposed side. The C-arm 12 is movable in several directions along multiple image acquisition paths, including, among others, an orbital tracking direction, longitudinal tracking direction, lateral tracking direction, transverse tracking direction, pivotal tracking direction, and "wig-wag" tracking direction. The orbital rotation direction is denoted by arrow A. FIG. 1 illustrates the C-arm 12 and receptor 34 in solid lines while located at a first position (P1), and in shadow lines while located at a second position (P2). Alternatively, the C-arm 12, receptor 34 and x-ray source 36 may be moved along image acquisition paths in the longitudinal, lateral, transverse and wig-way tracking directions and the like.

The tracker module 18 monitors the position of the patient 22, the receptor 34, and an instrument or tool 24 (if present) used by a doctor during a diagnostic or interventional surgical procedure. The tracker module 18 provides tracking component coordinates 26 with respect to each of the patient 22, receptor 34, and instrument 24 to the tracking data processor 20. The tracking data processor 20 uses the tracking component coordinates 26 to continuously calculate the positions of the receptor 34, patient 22 and instrument 24 with respect to a coordinate system defined relative to a coordinate system reference point. The reference point for the coordinate system is dependent, in part, upon the type of tracker module 18 to be used. The tracking data processor 20 sends control or trigger commands 28 to the x-ray generator 14 which in turn causes one or more exposures to be taken by the x-ray source 36 and receptor 34. The tracking data processor 20 provides exposure reference data 30 to the image processing computer 16. The control or trigger commands 28 and exposure reference data 30 are generated by the tracking data processor 20, as explained in more detail below, based on the tracking component coordinates 26 as the C-arm is moved along an image acquisition path.

Figure 2:
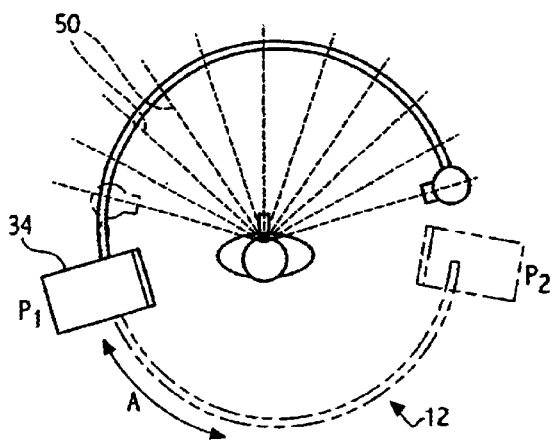
FIG. 2 illustrates a fluoroscopic imaging system using an electromagnetic tracking subsystem and is movable through a range of orbital rotation formed in accordance with a preferred embodiment of the present invention.

By way of example, the C-arm 12 may be manually moved between first and second positions P1 and P2 as a series of exposures are obtained. The image acquisition path may be along the orbital rotation direction (as shown in FIG. 2) and the receptor 34 may be rotated through a range of motion from 0 to 145° or from 0 to 190°. Alternatively, the image acquisition path may be along the lateral rotation direction denoted by arrow B in FIG. 3 between positions P3 and P4.

The image processing computer 16 collects a series of image exposures 32 from the receptor 34 as the C-arm 12 is rotated. The receptor 34 collects an image exposure 32 each time the x-ray source 36 is triggered by the x-ray generator 14. The image processing computer 16 combines each image exposure 32 with corresponding exposure reference data 30 and uses the exposure reference data 30 to construct a three-dimensional volumetric data set as explained below in more detail. The three-dimensional volumetric data set is used to generate images, such as slices, of a region of interest from the patient. For instance, the image processing computer 16 may produce from the volumetric data set saggital, coronal and/or axial views of a patient spine, knee, and the like.

Figure 6:
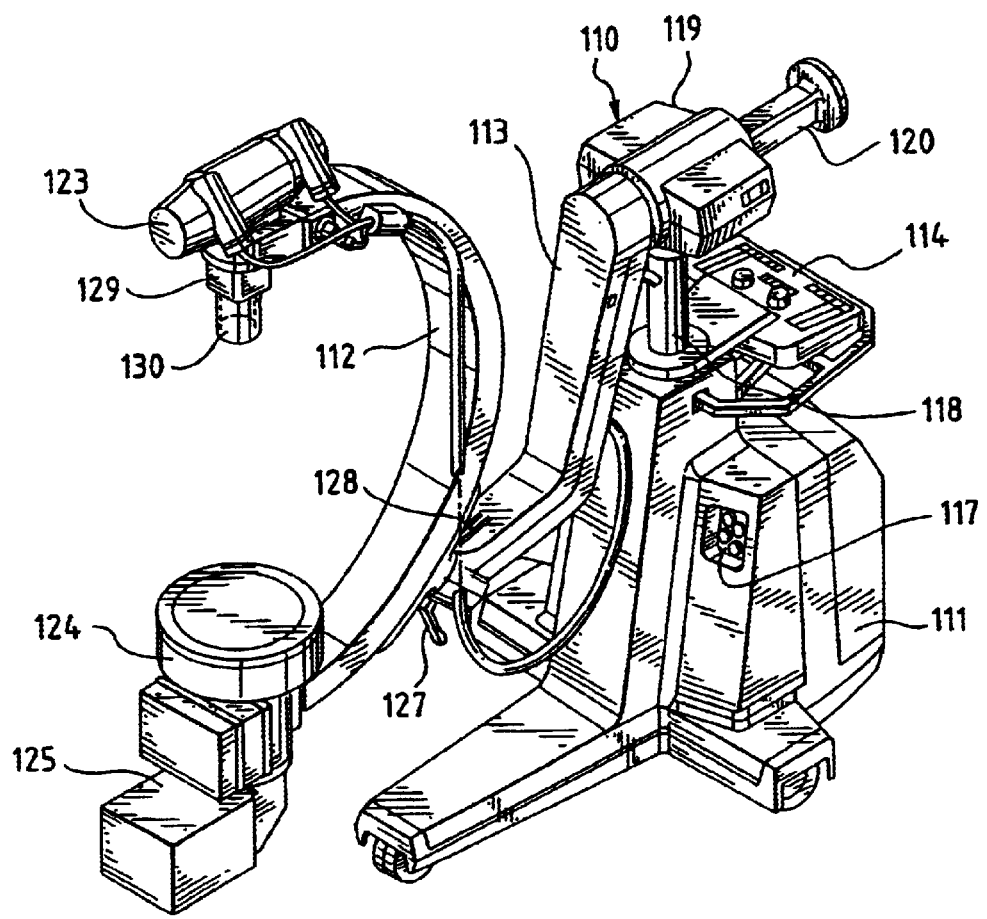
FIG. 6 illustrates a C-arm that may be used in accordance with one or more of the preferred embodiments of the present invention.

FIG. 6 illustrates an exemplary mobile C-arm x-ray unit 110. A principal function of the mobile C-arm x-ray unit 110 is to generate x-rays for diagnostic and interventional imaging. The unit 110 is comprised of a mainframe 111, a C-arm 112, an L-arm 113 and control panel 114. The lower portion of the mainframe 111 forms a T-shaped structure, wherein casters are utilized to provide mobility of the unit 110. The mainframe 111 includes a power panel 117 for controlling the coupling of power, as well as other devices, to unit 110. The mainframe 111 also includes a vertical lift column 118 that permits the C-arm 112 and L-arm 113 to move vertically in relation to mainframe 111. Vertical lift column 118 terminates in an upper housing 119, wherein horizontal extension arm 120 passes through upper housing 119 and permits arm 120 to move perpendicularly in relation to vertical lift column 118 by movement of the horizontal extension arm 120 in relation to upper housing 119. The C-arm 112 may be moved along the axis of the horizontal extension arm 120 to effect transverse tracking motion. The L-arm 113 is capable of pivoting (pivotal tracking motion) about the horizontal extension arm 120 such that the L-arm 113 can be made to pivot in a 360° arc. The horizontal extension arm 120 is coupled to one end of the L-arm 113, while the outer end of the L-arm 113 is coupled to C-arm 112.

The C-arm 112 is a C-shaped structure having an x-ray emitter 123 at one end of the C-arm 112 and a receptor, such an image intensifier 124 with a camera 125, at the other end of the C-arm 112. The C-arm 112 includes a flip-flop lock 128 and flip-flop brake 127 that permit a 180° rotation of the C-arm 112. A collimator assembly 129 may be provided for collimating the x-ray beam from the x-ray emitter 123. A spacer 130 provides a safety distance that a patient may be brought within the x-ray emitter 123.

The unit 110 is typically coupled to a monitoring unit wherein such monitoring unit includes equipment necessary for viewing the video image provided by the camera 125. The coupling is accomplished through cables coupled through power panel 117 of the unit 110 to the monitoring equipment, such as a video display monitoring cart, which is typically used in conjunction with C-arm x-ray unit 110. Alternatively, the monitoring equipment and video display monitoring card may be formed integral with the C-arm x-ray unit 110.

Returning to FIG. 1, the tracker module 18 receives position information from receptor, patient and instrument position sensors 40, 42 and 44, respectively. The sensors 40–44 may communicate with the tracker module 18 via hardwired lines, infrared, radio waves and the like. The sensors 40–44 and tracker module 18 may be configured to operate based on one of several known medium, such as electromagnetics, optics, infrared and the like. Alternatively, the sensors 40–44 and tracker module 18 may operate based on a combination of such medium.

By way of example only, in an electromagnetic (EM) implementation, a field transmitter/generator is provided with up to three orthogonally disposed magnetic dipoles (e.g., current loops or electromagnetics). The magnetic fields generated by each of the three dipoles are distinguishable from one another either through phase, frequency or time division multiplexing. The magnetic fields may be relied upon for position detection. The field transmitter/generator may form any one of the patient position sensor 42, receptor position sensor 40 or instrument position sensor 44. The field transmitter/generator emits EM fields that are detected by the other two of the position sensors 40–44. By way of example, the patient position sensor 42 may comprise the field transmitter/generator, while the receptor and instrument position sensors 40 and 44 comprise one or more field sensors each.

In an alternative embodiment, the sensors 40–44 and tracker module 18 may be configured based on optical or infrared signals. In an embodiment based on optics or infrared, a separate position monitoring camera 46 is added to monitor the position of the sensors 40–44 and to communicate with the tracker module 18. In this alternative embodiment, active infrared light may be periodically emitted by each sensor 40–44 and detected by the position monitoring camera 46. Alternatively, the sensors 40–44 may operate in a passive optical configuration, whereby separate infrared emitters are located at the camera 46 and/or about the room. The emitters are periodically triggered to emit infrared light. The emitted infrared light is reflected from the sensors 40–44 onto one or more cameras 46. The active or passive optical information collected through the cooperation of the sensors 40–44 and position monitoring camera 46 is used by the tracker module 18 define tracking component coordinates for each of the patient 22, receptor 34 and instrument 24. The position information may define six degrees of freedom, such as x, y, z coordinates and pitch, roll and yaw angular orientations. The position information may be defined in the polar or Cartesian coordinate systems.

In yet a further alternative embodiment, the tracker module 18, and sensors 40–44 may operate based on triangulation of signals, wherein the sensor 42 operates as a signal transmitter, while the sensors 40 and 44 operate as signals receivers. In a triangulation system, position detection is achieved by comparing characteristics of first and second transmitted signals to determine relative distances traveled. The transmitted signals may be ultrasonic or electromagnetic, such as radio waves, laser light, light emitting diodes and the like.

As a further alternative embodiment, a plurality of rf receiving coils may be placed about the subject, such as being attached to the receptor 34 as shown in U.S. Pat. No. 5,251,635. The surgical instrument 24 may be modified to incorporate a small rf transmit coil, with at least one coil on each tool or instrument 24 to determine the instrument's position and at least two coils per instrument to determine orientation. The tracker module 18 and tracking data processor 20 cooperate to calculate the position and orientation of the transmit coils and thus the instrument 24. The calculated position of the instrument 24 is displayed by superposition of a symbol on an x-ray image that appears on the video monitor 48. Sensor 42 on the patient 22 may be used in the manner described above to locate the position within the reference coordinate system. The reference coordinate system in the present exemplary embodiment is defined with the transmitter on the instrument 24 as the origin of the coordinate system. During operation, the tracking module 18 monitors the position of the instrument 24 and of the receptor 34 with respect to a coordinate system having an origin at the transmitter of the patient position sensor 42.

The tracker module 18 generates a continuous stream of tracking component coordinates, such as the Cartesian coordinates, pitch, roll and yaw for the instrument (I(x, y, z, pitch, roll, yaw)), for the detector 34 D(x, y, z, pitch, roll, yaw), and/or patient 22 P(x, y, z, pitch, roll, yaw). When the patient position sensor 42 is provided with an EM transmitter therein (in accordance with at least one preferred embodiment), the coordinate reference system may be defined with the origin at the location of the patient position sensor 42. When an infrared tracking system is used, the coordinate system may be defined with the point of origin at the patient monitoring camera 46.

The tracking data processor 20 continuously collects the stream of tracking component coordinates 26 and continuously calculates the position of the patient 22, receptor 34 and instrument 24 relative to a reference point. The tracking data processor 20 may calculate rotation positions of the C-arm and store each such position temporarily. Each new rotation position may be compared with a target position, representing a fixed angular position (defined in x, y, z coordinates within the coordinate system) or based on a fixed arcuate movement (e.g., 5° and the like). When a 3-D acquisition procedure is initiated, the tracking data processor 20 establishes a reference orientation for the C-arm 12. For instance, the tracking data processor 20 may initiate an acquisition process once the receptor 34 is moved to one end of an image acquisition path with beginning and ending points corresponding to a 0° angle and 190° angle, respectively. Alternatively, the tracking data processor 20 may initialize the coordinate reference system with the C-arm 12 located at an intermediate point along its range of motion. In this alterative embodiment, the tracking data processor 20 defines the present position of the receptor 34 (wherever that may be) as a starting point for an acquisition procedure. Once the tracking data processor 20 establishes the starting or initial point for the image acquisition procedure, a control/trigger command 28 is sent to the x-ray generator 14 and initial exposure reference data 30 is sent to the image processing computer 16. An initial image exposure 34 is obtained and processed.

After establishing an initial position for the receptor 34, the tracking data processor 20 continuously monitors the tracking component coordinates 26 for the receptor 34 and determines when the receptor 34 moves a predefined distance. When the tracking component coordinates 26 indicate that the receptor 34 has moved the predefined distance from the initial position, the tracking data processor 20 sends a new control or trigger command 28 to the x-ray generator 14 thereby causing the x-ray source 36 to take an x-ray exposure. The tracking data processor 20 also sends new exposure reference data 30 to the image processing computer 16. This process is repeated at predefined intervals over an image acquisition path to obtain a series of images. The image processing computer 16 obtains the series of image exposures 32 that correspond to a series of exposure reference data 30 and combines same into a volumetric data set that is stored in memory.

By way of example, the tracking data processor 20 may cause the x-ray generator 14 and image processing computer 16 to obtain image exposures at predefined arc intervals during movement of the receptor 34 around the orbital path of motion. The orbital range of motion for the receptor 34, over which images are obtained, may be over a 145° range of motion or up to a 190° range of motion for the C-arm 12. Hence, the receptor 34 may be moved from a zero angular reference point through 145° of rotation while image exposures 32 are taken at predefined arc intervals to obtain a set of image exposures used to construct a 3-D volume. Optionally, the arc intervals may be evenly spaced apart at 1°, 5°, 10° and the like, such that approximately 100, 40, or 15, respectively, image exposures or frames are obtained during movement of the detector 34 through rotation. The arc intervals may be evenly or unevenly spaced from one another.

The receptor 34 may be manually moved by the operator at any desired speed. The operator may also move the receptor 34 at an increasing, decreasing or otherwise uneven velocity since exposures are triggered only when the receptor 34 is located at desired positions that are directly monitored by the tracker module 18.

Figure 3:
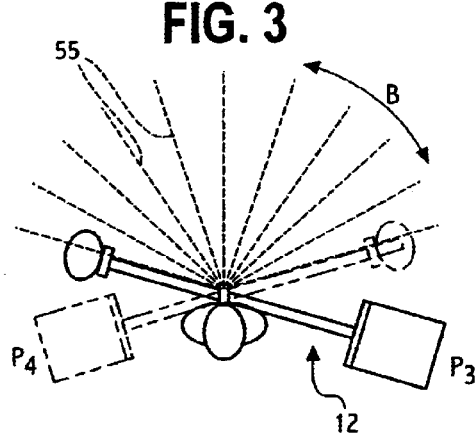
FIG. 3 illustrates a fluoroscopic imaging system that uses an electromagnetic tracking subsystem and that is movable through a range of lateral rotation formed in accordance with the preferred embodiment of the present invention.

FIGS. 2–3 illustrate two exemplary ranges of motion for the C-arm 12. In the example of FIG. 2, the C-arm 12 is moved through a range of orbital motion manually or automatically to obtain discrete exposures at desired intervals (e.g., exposure intervals 50) in order to construct a 3-D patient data set. In the example of FIG. 3, the C-arm 12 may be moved in a different direction from orbital rotation, namely the C-arm 12 may be moved through a range of lateral rotation. At discrete angles along the range of lateral motion indicated by the dashed lines 55, exposures may be obtained in the manner explained above to construct a 3-D patient data set.

Figure 4:
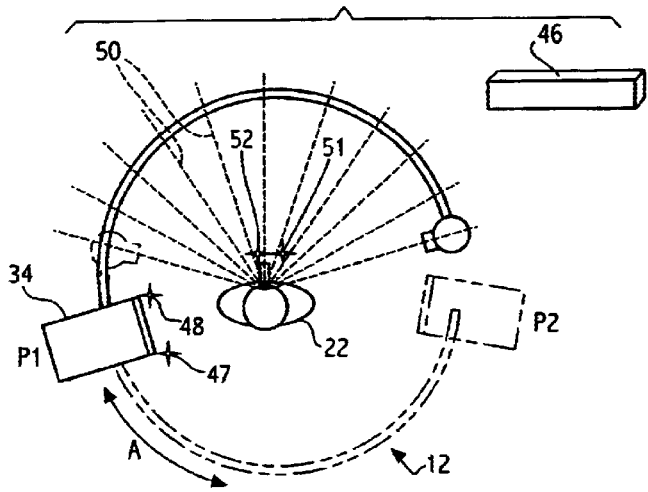
FIG. 4 illustrates a fluoroscopic imaging system that uses an optical tracking subsystem and that is movable through a range of orbital rotation formed in accordance with a preferred embodiment of the present invention.
Figure 5:
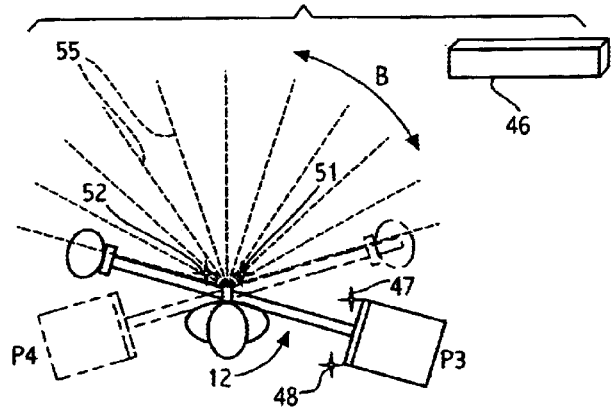
FIG. 5 illustrates a fluoroscopic imaging system that uses an optical tracking subsystem and that is movable through a range of lateral rotation formed in accordance with a preferred embodiment of the present invention.

FIGS. 4–5 illustrate a range of orbital rotation and lateral rotation, respectively, through which the receptor 34 may be moved, similar to the ranges of motion in FIGS. 2–3. In the example of FIGS. 4–5, an optical tracking system is used having a camera 46 to detect the position of LEDs 47 and 48 on the receptor 34 and LEDs 51 and 52 on the patient 22. Optionally, LEDs 47, 48, 51 and 52 may be passive reflectors.

Figure 7:
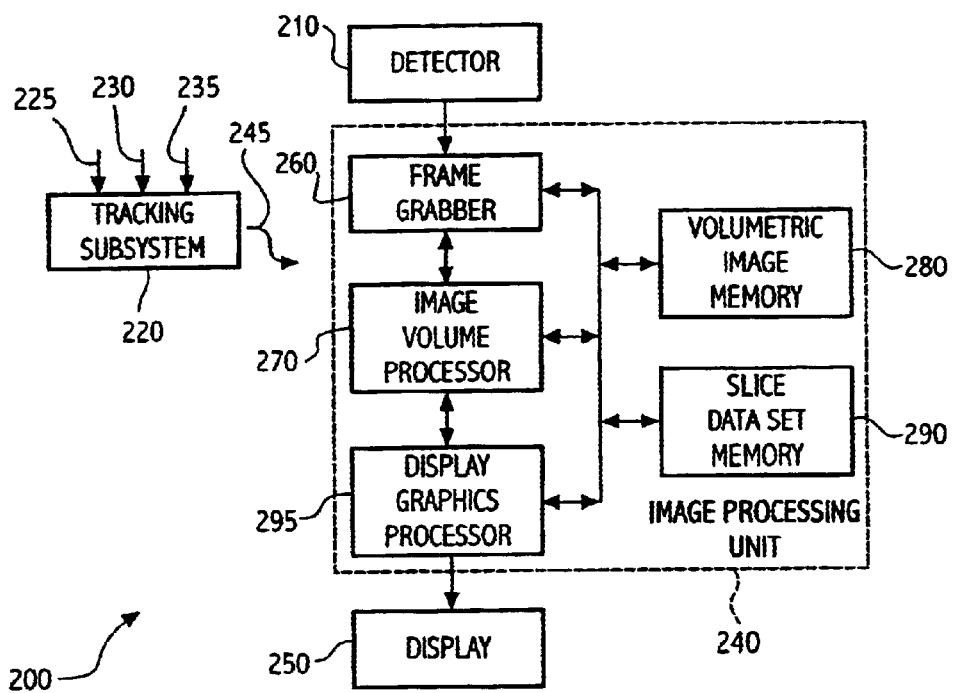
FIG. 7 illustrates a block diagram of an alternative embodiment of the present invention.

FIG. 7 illustrates an alternative embodiment formed in accordance with the present invention. A fluoroscopy imaging system 200 includes a detector 210 mounted to a C-arm for detecting x-rays passed through a patient. A tracking subsystem 220 receives patient coordinate information 225, detector coordinate information 230 and instrument coordinate information 235. The tracking subsystem 220 processes the coordinate information 225–235 and passes it to an image processing unit 240 which receives exposure frames from the detector 210 and outputs image frames to the display 250. The image processing unit 240 includes a frame grabber 260 which collects exposure frames from the detector 210 at points in time dictated by the position data 245 provided from the tracking subsystem 220.

The exposure frames are passed from the frame grabber 260 to the image volume processor 270 which manages storage of exposure frames in a volumetric image memory 280. The image volume processor 270 constructs a three-dimensional patient data volume in the volumetric image memory 280. The 3-D patient data volume may be constructed based upon very few exposure frames, such as 10 and the like. As additional exposure frames are obtained by the frame grabber 270, the accuracy and completeness of the 3-D patient data volume is improved. In addition to constructing the 3-D patient data volume, the image volume processor 270 also constructs image slices from the volume. The slices are stored in the slice data set memory 290.

The display graphics processor 295 accesses the slice data set memory 290 to display the image slices on the display 250. The display graphics processor 295 also constructs graphical representations of the instrument or tool 24 and overlays the instrument graphic with the image slices on the display 250. The display graphics processor 295 may present multiple two-dimensional image slices simultaneously on the display 250 with instrument graphics superimposed upon each image slice. Alternatively or in combination with image slices, the display graphics processor 295 may construct a three-dimensional rendering of the 3-D patient data volume and display the three-dimensional rendering on the display 250 separately or in combination with a three-dimensional graphical representation of the instrument 24. The three-dimensional patient image and three-dimensional instrument graphic may be controlled to rotate (in a video-type format) to permit viewing of the patient data volume from multiple angles and to permit viewing of the instrument graphic from multiple angles. Rotation of the three-dimensionally displayed patient data volume may be automatic, such as in a simulated video format, or may be controlled manually in a stepwise manner by the operator of the system. For example, the operator may rotate the image (s) by clicking on the region of interest with a mouse and drag the image to cause rotation and/or translation.

FIG. 8 illustrates a general processing sequence followed by at least one preferred embodiment of the present invention in connection with obtaining and displaying fluoroscopic information and instrument or tool information. Beginning at step 300, the receptor 34 obtains an initial exposure and the tracker module 18 and tracking data processor 20 initialize the image receptor 34 position. The initial position of the image receptor 34 may represent a point at one extreme of the rotational orbit of the receptor 34 about the C-arm 12. Alternatively, the initial position for the image receptor 34 may merely represent the present position at the time that an operator initiates a 3-D acquisition operation. Once the initial exposure and receptor 34 position are obtained at step 300, flow passes to step 305 at which the position of the receptor 34 is continuously monitored by the tracking module 18 and tracking data processor 20.

Once the receptor 34 moves a desired distance from the most recent prior position at which an exposure was obtained, flow passes to step 310. At step 310, the tracking data processor 20 causes the x-ray generator 14 to trigger the x-ray source 36 to obtain a new exposure. The tracking data processor 20 at step 315 directs the image processor 16 to capture a new exposure from the receptor 34. The image processing computer 16 captures the new exposure and, at step 320, stores the new exposure along with the position of the receptor 34, where the position information is provided from the tracking data processor 20. The new exposure obtained at step 315 is used at step 325 by the image processing computer 16 to update the 3-D patient data set. At step 335, the image processing computer 16 constructs patient slices and/or a three-dimensional image of the 3-D patient data set.

Preferably, the 3-D patient data set is updated with the information from 10 or more exposures before patient slices are reconstructed. Additional exposures may be obtained, beyond 10 exposures by repeating steps 305–325, thereby improving the information within the 3-D patient data set. Once patient slices and/or 3-D images are constructed at step 335, the patient slices and/or 3-D images are displayed at step 340, alone or in combination with instrument graphics representing the position of the instrument 24 relative to the patient 22. Dashed lines 330, 345 and 350 indicate that, while steps 325, 335 and 340 are being carried out, the image processing computer 16 performs parallel operations to repeat steps 305–340 to improve upon the 3-D patient data set and also upon the patient slices and 3-D images being displayed.

Returning to FIG. 1, by way of example only, a series of dashed lines 50 are illustrated representing discrete positions at which exposures may be obtained for use in constructing the 3-D patient data set. Optionally, the image capture positions 50 may be evenly divided, such as at 5° intervals and the like, along at least a portion of the orbital rotation of the receptor 34. For example, the receptor 34 may be moved along a 145° arc of orbital rotation, while obtaining exposures every 5°.

As a further alternative, the receptor 34 may be moved through a portion of, or the entire, range of motion of the C-arm 12 (orbital, longitudinal, transverse, pivotal or otherwise) more than once during collection of the 3-D patient data set. For example, the doctor may move the receptor 34 through a 145° orbital rotation in a first direction and through a 145° orbital rotation in the opposite direction, during both of which the receptor 34 obtains exposures. The exposures obtained during motion of the receptor 34 in both directions may be at the same angular positions or at different positions interleaved with one another (e.g., at 0, 10, 20° angles, etc. when moving in the first direction and at 25°, 15°, 5° angles and the like when moved in the opposite direction).

As a further alternative, when the patient slices and/or images are reconstructed at step 335 and/or displayed at step 340, holes in the data set may be identified (e.g., regions for which very little or no data are known). These holes may appear as black areas on the display. Holes in the data set may be identified manually by the physician while displaying the slices at step 340. Alternatively, the system may automatically identify holes in the data set at step 335. Once holes in the data set are located, the receptor 34 may be moved automatically or manually through a smaller portion of the overall image acquisition path to obtain additional data to fill in the holes in the 3-D patient data set. Optionally, if holes in the patient data set are identified at step 335, the image processing computer 16 may inform the tracking data processor 20 of the region for which more data is needed and, in response thereto, the tracking data processor 20 may only obtain additional exposures (through control of the x-ray generator 14) at certain discrete orbital angles for the receptor 34. For example, if the image processing computer 16 determines at step 335 that further exposures are needed for a region of interest associated with the 40–60° angular positions of the receptor 34, the image processing computer 16 may instruct the tracking data processor 20 to monitor the position information of the receptor 34 from the tracking module 18 and only trigger additional exposures when the receptor 34 is moved through the 40–60° orbital range (if at all). The operator may move the receptor 34 through a larger angular range (e.g., 10°–90°), but the receptor 34 will only take new exposures at the desired angular positions (e.g., 40°–60°).

Alternatively, the operator may identify holes in the data set while displaying slices and/or 3-D images at step 340. In this instance, the operator may manually enter a range of orbital positions at which new exposures should be obtained. For example, the user may inform the tracking data processor 20 that new exposures should be obtained between orbital angles 120°–170°. Thereafter, the tracking data processor 20 will monitor the position information from the tracker module 18 and only trigger the x-ray source 36 when the receptor 34 is moved through the manually entered orbital range of interest.

The 3-D patient data set may be constructed in step 325 using any one of several algorithms known for constructing three-dimensional data volumes based upon exposures obtained from a cone beam source. By way of example, the 3-D patient data set may be constructed at step 325 using any one of several well known techniques, such as forward and/or back projection techniques. The patient slices and 3-D images constructed in step 335 may be created in accordance with any of several known algorithms such as those used in connection with existing CT systems. The 3-D images constructed at step 335 and displayed at step 340 may be created from the 3-D patient data set based upon any one of several known volume rendering techniques, such as ray casting and the like. Several known techniques exist for constructing data sets of patient slices (such as for sagittal, coronal and axial patient views), segments and 3-D rendered images.

The number of exposures collected in steps 305–325 will determine the amount of time needed to reconstruct patient slices at step 335. For instance, if 40 frames are obtained to construct the 3-D patient data set, it may take up to 14 minutes to reconstruct a set of patient slices therefrom. The patient slices may be constructed more quickly if fewer frames are obtained and more slowly if more than 40 frames are obtained.

Optionally, the image processing computer 16 may perform frame averaging, whereby the receptor 34 obtains more than one exposure at each angular position and averages such frames before using the averaged frame to update the 3-D patient data set. Preferably, however, the image processing computer 16 may only use one exposure obtained by the receptor 34 at each orbital rotation. When a single exposure is obtained at each orbital rotation, the x-ray generator 14 is controlled to generate a higher energy x-ray dose. For instance, when frame averaging is used, a low dose (e.g., 40 mA) may be used, whereas when a single exposure is obtained at each orbital rotation, a high dose (e.g., 150 mA and the like) may be used. In certain instances, it may be preferable to use high energy doses, such as used in cardiac applications, to obtain high quality images, without averaging.

When generating high energy doses, shorter pulse lengths may be used as compared to when performing low energy doses. For example, when a single exposure is obtained at each orbital rotation of the receptor 34, the x-ray generator 14 may be controlled to provide a high energy short pulse of between 3 and 6 ms. During frame averaging, the x-ray generator 14 may provide a low energy longer pulse, such as up to 20 ms or more. In certain applications, it may be preferable to obtain a single exposure from the receptor 34 at each orbital rotation to avoid blurring that may be caused by averaging two or more frames that are obtained at close, but not the exact same position by the receptor 34.

Optionally, the receptor 34 may include an image intensifier used in combination with a viticon-type scanning camera. Alternatively, the receptor 34 may include an image intensifier used in connection with a CCD detector-type camera. Optics are typically provided between the image intensifier and the camera to afford a more compact receptor 34. As a further alternative, the receptor 34 may be constructed with a flat panel detector, thereby entirely removing the use for an image intensifier or camera.

In certain preferred embodiments, the receptor 34 is described as being manually moved by the operator. Manual movement is supported since the tracking subsystem determines the absolute position of the receptor 34 with respect to a coordinate system including both the instrument 24 and patient 22. Manually moving the receptor 34 avoids the need for the additional structure associated with automatic control of the receptor 34. Using a tracking system that detects the absolute position of the receptor 34, instrument 24 and patient 22 within a common coordinate system and from such information triggering exposures, renders the speed and acceleration rate of the receptor 34 irrelevant. Hence, the rate at which the receptor 34 is moved does not change the accuracy or quality of images.

As an alternative embodiment, the tracking system including tracker module 18 and tracking data processor 20 need not monitor the position of the receptor 34. Instead, a series of sensors may be located about the C-arm 12 to detect orbital rotation, longitudinal rotation, lateral rotation, movement of the L-arm, transverse movement, the "wig-wag" movement and the like. The series of sensors, by monitoring all points of movement within the C-arm relative to a reference point, such as a point in the room, a point on the patient, or a point on the instrument, may be used to control the time at which exposures are obtained and enable a sequence of exposures to be obtained along a plurality of image acquisition paths in addition to the paths illustrated in FIGS. 1–5.

As a further alternative, the C-arm 12 may build a composite volume data set extending along a patient over an area larger than the receptor 34, such as along the spine of a patient. Multiple sets of exposures may be taken to build a rectangular volume encasing a region of interest, such as the complete spine, a complete leg, and the like. By way of example, the C-arm may be positioned proximate to the base of the spine and moved through an orbital rotation range of motion to obtain a first set of data. Typically, the receptor 34 is able to collect data for an area of up to 9 to 12 inches in diameter depending upon the magnification effect caused by the patient's proximity to the x-ray source 36. Once the first series of exposures is obtained, the C-arm 12 may be moved along the spine by an amount less than 9 to 12 inches, such that the new C-arm 12 position slightly overlaps the initial position of the C-arm 12. Once repositioned, the C-arm may be moved around a new orbital rotation to obtain a second series of image exposures. This process may be again repeated if needed for a third set of image exposures until information regarding the complete spine is obtained. The first, second (and if needed third) sets of exposures for the spine may be combined to construct a rectangular volume, from which slides are obtained.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

What is claimed is:

1. A medical imaging system, comprising:
   a C-arm unit having an x-ray source for generating x-rays and a receptor for obtaining image exposures from received x-rays, the C-arm capable of moving the x-ray source and receptor along an image acquisition path between at least first and second exposure positions;
   a position detector for monitoring the position of the receptor and the position of a patient and producing position data;
   an acquisition module for collecting a series of image exposures from the receptor including at least first and second image exposures obtained while said receptor is located at said first and second exposure positions, respectively, said acquisition module collecting said series of image exposures based on said position data from said position detector;
   an image processor for constructing a three dimensional (3D) volumetric data set based on said series of image exposures and said position data; and
   a display for displaying images from at least one of a plurality of angles based on said three dimensional volumetric data set.

2. The medical imaging system of claim 1, wherein said image processor constructed a computed tomography volume.

3. The medical imaging system of claim 1, further comprising:
   a base, said C-arm being rotatably mounted to said base, said base moving said C-arm along said image acquisition path that constitutes an orbital rotation path in which the x-ray source and receptor are rotated along a lane including the C-arm with respect to a patient between said first and second exposure positions.

4. The medical imaging system of claim 1, further comprising:
   a lateral rotation unit connected to said C-arm, said lateral rotation unit moving said C-arm along a lateral rotation path forming at least part of said image acquisition path to move said receptor between said first and second exposure positions.

5. The medical imaging system of claim 1, further comprising:
   a pivot member connected to said C-arm, said pivot member pivoting said C-arm about a pivot axis extending along a plane containing said C-arm, said pivot member pivoting said receptor about a pivotal image acquistion path between at least said first and second exposure positions.

6. The medical imaging system of claim 1, wherein said image processor transforms multiple 2D fluoroscopic images into 3D volumetric data sets.

7. The medical imaging system of claim 1, wherein said image processor performs an iterative reconstruction technique to construct 3D volumetric data set.

8. The medical imaging system of claim 1, wherein said image processor performs one of a back projection and a forward projection technique to construct said 3D volumetric data set.

9. The medical imaging system of claim 1, wherein said acquisition module acquires a sequence of 2D fluoroscopic images at positions evenly spaced along said image acquisition path.

10. The medical imaging system of claim 1, wherein said acquisition module continuously calculates a position of the C-arm with respect to a coordinate reference system and triggers said x-ray source to generate x-rays when said C-arm reaches predetermined positions along said image acquisition path.

11. The medical imaging system of claim 1, wherein said first and second exposure positions constitute beginning and ending positions, respectively, along an arcuate range of motion of said C-arm, aid beginning and ending positions being no more than 190° apart.

12. The medical imaging system of claim 1, wherein said acquisition module obtains 2D fluoroscopic images at an even interval along said image acquisition path, said even interval being no more than 5° of rotation of said C-arm.

13. The medical imaging system of claim 1, wherein said acquisition module obtains no more than 40 image exposures to be used by said image processor to construct said 3D volumetric data set.

14. The medical imaging system of claim 1, wherein said image processor constructs said 3D volumetric data set from no more than 20 image exposures.

15. The medical imaging system of claim 1, further comprising:
   a tracking module for obtaining position coordinates of said receptor with respect to a reference coordinate system having an origin at a fixed point on a patient and a tracking data processor obtaining said exposure images based on said position coordinates identifying a position of said receptor relative to the patient.

16. The medical imaging system of claim 1, wherein said C-arm is manually moved along said image acquisition path.

17. The medical imaging system of claim 1, further comprising a tracker module that continuously obtains tracking component coordinates for said receptor, tracking component coordinates for patient and tracking component coordinates for a surgical instrument.

18. A method for constructing a three-dimensional (3D) volumetric data set from image exposures of a patient obtained by a C-arm fluoroscopic apparatus, the method comprising:
   moving a C-arm unit along an image acquisition path relative to a patient;
   continuously electronically monitoring a position of the C-arm unit and a position of the patient;
   obtaining a series of image exposures of the patient as the C-arm unit is moved along said image acquisition path when the C-arm unit is positioned at predetermined exposure positions with respect to the patient position, wherein said series of image exposures is obtained based on the position of the C-arm unit with respect to the patient; and
   constructing a 3D volumetric data set from aid series of image exposures, said 3D volumetric data set including data to generate a least one of a patient view slice, a patient view segment, and a patient view volume from at least one viewing angle.

19. The method of claim 18, further comprising triggering an x-ray source and directing a receptor to obtain image exposures when the receptor on the C-arm unit reaches predefined orbital positions with respect to the patient.

20. The method of claim 18, further comprising continuously generating tracking component coordinates identifying the position of the patient and the position of the C-arm unit in a coordinate reference system having an origin at a fixed point on the patient, said obtaining step initiating each image exposure based on said tracking component coordinates.

21. The method of claim 18, further comprising manually moving the C-arm unit along said image acquisition path.

22. The method of claim 18, further comprising automatically moving C-arm unit along said image acquisition path.

23. The method of claim 18, wherein said moving step directs an x-ray source and receptor on the C-arm unit along one of an orbital rotation direction, a longitudinal direction, a transverse direction, a pivotal direction and a wig-wag direction.

24. The method of claim 18, wherein said monitoring step includes optically detecting the position of the C-arm unit and the position of the patient.

25. The method of claim 18, wherein said monitoring step includes detecting the position of the C-arm unit and the position of the patient based on electromagnetic signals transmitted from one of the patient and C-arm unit and detected at a sensor on the other of the patient and the C-arm unit.

26. The method of claim 18, further comprising detecting the position of a surgical instrument and displaying a graphical representation of the instrument superimposed on images generated from the 3D volumetric data set.

27. The method of claim 18, wherein said obtaining step obtains image exposures at 5° intervals along an orbital rotation defining said image acquisition path.

28. A method for using a digital fluoroscopic system to form a patient data set and generate patient view slices from the patient data set, the method comprising:
   moving an x-ray detector through a range of motion between starting and ending positions relative to a patient;
   tracking a position of the detector relative to the patient;
   triggering a series of exposures by the detector based on the position of the detector relative the patient;
   storing each image exposure with position tracking data identifying the position of the detector within a reference coordinate system to form a patient data set; and
   generating at least one of a plurality of patient view slices, a patient view segment, and a patient view volume from the patient data set.

29. The method of claim 28, further comprising manually moving the x-ray detector.

30. The method of claim 28, further comprising generating and displaying saggital, coronal, and axial view slices of the patient from the patient data set.

31. The method of claim 28, further comprising performing iterative back projection to construct a volumetric data set from the series of image exposures.

32. The method of claim 28, further comprising, while moving the x-ray detector in a first direction, obtaining a first portion of the series of image exposures and, while moving the x-ray detector in second direction, obtaining a second portion of the series of image exposures, said first and second directions differing.

33. The method of claim 32, wherein said first and second directions are opposite to one another.

34. The method of claim 32, wherein said first portion constitutes a first half of said series of image exposures and said second portion constitutes a second half of said series of image exposures.

* * * * *

UNITED STATES PATENT AND TRADEMARK OFFICE
CERTIFICATE OF CORRECTION

PATENT NO. : 6,666,579 B2  
DATED : December 23, 2003  
INVENTOR(S) : Jensen

It is certified that error appears in the above-identified patent and that said Letters Patent is hereby corrected as shown below:

Column 8,  
Line 35, after the word "instrument" delete "("  
Line 36, after the first ")" delete ")"

Column 15,  
Line 21, delete "aid" and substitute therefor -- said --.  
Line 65, delete "aid" and substitute therefor -- said --.

Column 16,  
Line 47, after the word "relative" insert -- to --.

Signed and Sealed this

Second Day of November, 2004

JON W. DUDAS  
*Director of the United States Patent and Trademark Office*